United States Patent [19]
Tripp, Jr.

[11] Patent Number: 5,611,671
[45] Date of Patent: Mar. 18, 1997

[54] PUMPING SYSTEM FOR GROUNDWATER SAMPLING

[76] Inventor: Ralph N. Tripp, Jr., P.O. Box 364, Westfield, N.J. 07091-0364

[21] Appl. No.: 638,191

[22] Filed: Apr. 26, 1996

[51] Int. Cl.⁶ .................................................. F04B 1/06
[52] U.S. Cl. .......................... 417/126; 417/118; 417/149
[58] Field of Search .................................... 417/118, 137, 417/144, 149, 126, 130

[56] References Cited

U.S. PATENT DOCUMENTS

| | | |
|---|---|---|
| 8,834 | 5/1835 | Curtis ....................................... 417/118 |
| 298,990 | 5/1884 | Leedy ....................................... 417/118 |
| 3,814,545 | 6/1974 | Waters . |
| 3,963,377 | 6/1976 | Elliott et al. . |
| 3,991,825 | 11/1976 | Morgan ................................. 417/118 X |
| 4,489,779 | 12/1984 | Dickinson et al. . |
| 5,004,405 | 4/1991 | Brestin . |
| 5,183,391 | 2/1993 | Fiedler ................................ 417/126 X |

FOREIGN PATENT DOCUMENTS 426769  11/1947  Italy ......................................... 417/118

Primary Examiner—Richard E. Gluck
Attorney, Agent, or Firm—Norman B. Rainer

[57] ABSTRACT

A pump assembly for the accurate transfer of water to an above ground elevation includes a tubular housing having an upper extremity equipped with a gas inlet port, and a lower extremity equipped with a water inlet port having a first check valve. A second check valve divides the housing into upper and lower chambers. A sampling port located within the lower chamber communicates with a conduit that extends to an above-ground elevation. A third check valve, disposed within the conduit, permits upward flow but not downward flow of water in the conduit. A pumping apparatus is provided by combining the pump assembly with a gas controller located above ground level and which supplies gas at controlled pressure, volume and timed intervals to the gas inlet port.

10 Claims, 2 Drawing Sheets

PUMPING SYSTEM FOR GROUNDWATER SAMPLING

BACKGROUND OF THE INVENTION

1. Field of the Invention

This invention relates to the removal of fluids from wells, and more particularly concerns apparatus for retrieving water specimens under conditions which prevent alteration of the specimen.

2. Discussion of the Prior Art

The quality of naturally occurring water is a matter of increasing concern. Various toxic pollutant substances find their way into aquifer systems which may involve interconnected bodies of water such as lakes, rivers, bays and reservoirs. The toxic species may derive from industrial effluents, human wastes or natural factors of geological weathering, aging and erosion. The primary means of intercommunication of bodies of water within a single aquifer system is groundwater, namely water that flows underground at depths between about 15 and 150 feet.

In assessing the nature, cause and magnitude of pollution of an aquifer system, it is important to monitor associated groundwater at numerous sites. Because the characteristics of the groundwater usually varies with time, repetitive sampling is necessary.

Certain characteristics of water, such as pH, conductivity and redox potential can be monitored by detectors which provide continuous telemetering of data to a location remote from the monitored site. However, in most instances, more complete data is needed which can only be obtained by the grabbing of samples and transport of the samples to a full service analytical laboratory. In particular, the samples may be tested for toxic heavy metals by way of atomic absorption analysis, and toxic organics may be determined by way of gas chromatography/mass spectrometry analysis.

In order to accurately evaluate groundwater samples taken from a well, it is important to prevent changes from occurring in the water sample. The seemingly innocuous manipulation of pouring a water sample into a holding container can, for several reasons, destroy the validity of the sample. One of the involved reasons is that highly volatile species such as trichlorethylene and other low molecular weight carcinogens, dangerous at concentrations as low as 30 ppb, can quickly transfer from the water to the gas phase above the water. This is a partition effect, the rate and magnitude of which is governed by Raoult's law of physics. In the standard analytical procedure for volatile species, EPA Method SW846, it is stated in paragraph 4.1.2: "When collecting the samples, liquids should be introduced into the vials gently to reduce agitation which might drive off volatile compounds. Liquid samples should be poured into the vial without introducing any air bubbles within the vial as it is being filled. Should bubbling occur as a result of violent pouring, the sample must be discarded." Another undesired effect in the handling of groundwater samples is that oxygen from air may enter an otherwise anaerobic water sample.

Numerous techniques are known for the lifting of liquids such as water or oil from deep wells for sampling or production purposes. A number of such techniques involve the use of compressed gas. For example, U.S. Pat. No. 4,489,779 to Dickinson, et. al. discloses a gas-activated pump apparatus for withdrawing samples of groundwater from a well. The Dickinson pump employs a flexible bladder disposed within a valved housing. Sequentially pulsed expansions of the bladder drive water upwardly from said housing. U.S. Pat. No. 3,963,377 to Elliot, et. al. discloses a bladder-type pump somewhat similar to that of Dickinson. A complicating aspect of such bladder-type devices is that the pulsed expansions of the bladder require equipment components which permit expulsion of air from the bladder while creating a pressure differential between the interior of the bladder and the enveloping housing.

U.S. Pat. No. 5,004,405 to Breslin discloses a pump for use within a well casing, and employs a valved cylinder wherein compressed gas and liquid admitted to the top of the cylinder function as a piston to drive liquid in the bottom of the cylinder upwardly through a centered stored pipe. The compressed gas and liquid are in direct interfacial contact within the cylinder. U.S. Pat. No. 3,814,545 to Waters concerns a pump for delivering oil upwardly from a well, and utilizes a cylinder wherein a pressurized upper fluid of low density serves in piston-like manner in direct interfacial contact with the oil. The aforesaid pumps rely upon the hydrostatic pressure of the pumped liquid to fill a pumping chamber.

In certain sampling wells, particularly those of relatively shallow depth, there is insufficient hydrostatic pressure of the pumped water to achieve self-filling of a pumping chamber. In order to provide adequate driving force to transfer such water into a pumping chamber, an augmenting pressure gradient is needed such as may be produced by creating a negative pressure within the pumping chamber. However, if the water is exposed to a low pressure gas interface, volatile pollutants would escape from the water being sampled.

In order to remove meaningful samples from wells that have been stagnant for long periods of time, it is necessary to initially remove the stagnant water. Such removal often necessitates the pumping of large volumes of water. It is therefore desirable that any pump used for the accurate removal of sample quantities also has the ability to pump large volumes for disposal purposes.

It is accordingly an object of the present invention to provide a pump apparatus for the controlled delivery of water to above-ground elevation.

It is another object of this invention to provide a pump as in the foregoing object which accurately preserves the composition of groundwater for sampling purposes.

It is a further object of the present invention to provide a pump of the aforesaid nature which is actuated by a compressed gas but prevents direct interfacial contact of the gas with the delivered water.

It is a still further object of this invention to provide a pump apparatus of the aforesaid nature capable of augmenting hydrostatic forces in admitting groundwater into said pump.

It is an additional object of the present invention to provide a pump apparatus capable of handling large volumes of water for the disposal thereof, and small volumes of water for sampling purposes.

It is yet another object of this invention to provide apparatus of the aforesaid nature of simple, rugged construction amenable to low cost manufacture.

These objects and other objects and advantages of the invention will be apparent from the following description.

SUMMARY OF THE INVENTION

The above and other beneficial objects and advantages are accomplished in accordance with the present invention by a pump assembly for the accurate transfer of water to an above ground elevation comprising:

a) a tubular housing bounded by interior and exterior cylindrical surfaces and upper and lower extremities, b) a gas inlet port associated with said upper extremity, and a gas conduit communicating between said gas inlet port and an above-ground location, c) a groundwater inlet port associated with said lower extremity, and a first check valve associated with said inlet port and adapted to permit entrance of groundwater from said well upwardly into said housing, d) a second check valve disposed within said housing above said first check valve in a manner to divide said housing into an upper, actuating chamber bounded by said upper extremity and second check valve, and a lower, sample accumulating chamber bounded by said first and second check valves, said second check valve comprised of a seat member associated with the interior surface of said housing and a floating member, e) a sampling port located within said lower chamber and communicating with a water-conveying conduit that extends to an above-ground location, and f) a third check valve disposed within said water-conveying conduit in a manner to permit upward flow but not downward flow of water within said water-conveying conduit.

In a further aspect of the present invention, a pumping apparatus is provided comprised of the aforesaid pump assembly in combination with a gas controller member located above ground level and interactive with said gas conduit to supply a gas at controlled pressure, volume and timed intervals to the upper chamber of said housing.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
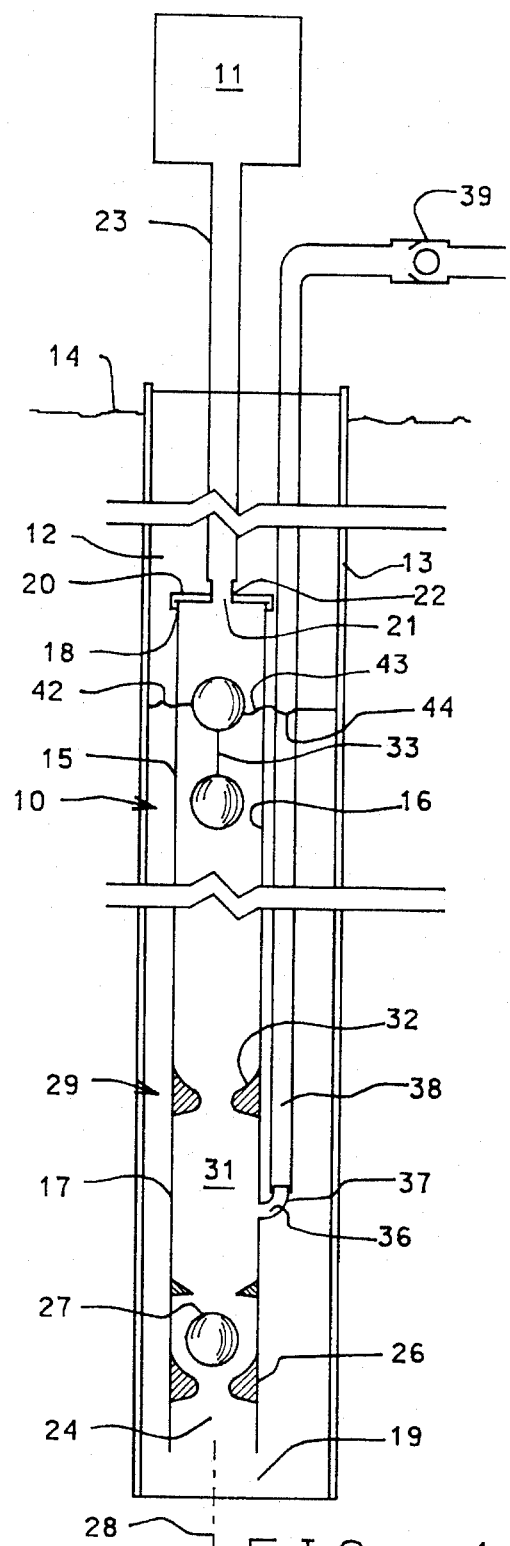
FIG. 1 is a vertical sectional view of an embodiment of the pumping apparatus of the present invention shown in functional association with a well, and in a sample-receiving stage of its cyclical operation.
Figure 2:
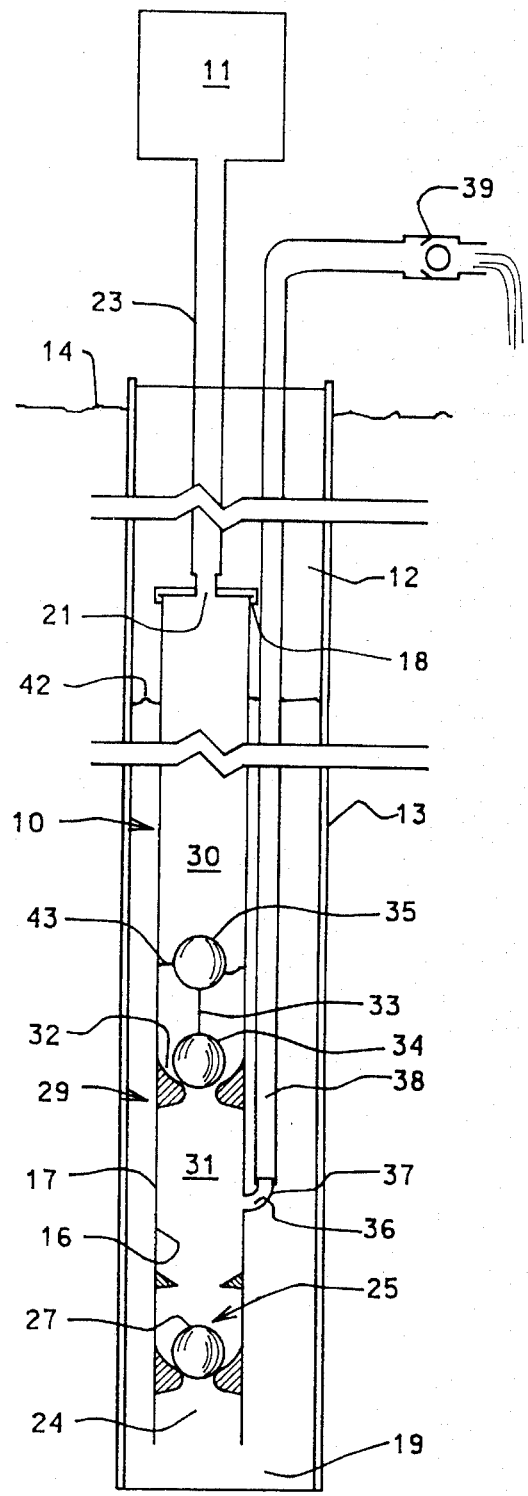
FIG. 2 is a view similar to that of FIG. 1 showing the apparatus in a sealed stage and ready to repeat the sample-receiving stage of cyclical operation.

Referring to FIGS. 1 and 2, an embodiment of the pumping apparatus of the present invention, comprised of pump assembly 10 and gas controller 11, is shown in functional association with a well 12 having cylindrical casing 13. Said pump assembly is disposed within casing 13, and said gas controller is located above ground level 14. Casing 13 may typically have a diameter between about 0.5 and 5 inches, and a length between about 10 and 100 feet.

Pump assembly 10 is comprised of a tubular housing 15 elongated upon center axis 28 and bounded by interior and exterior cylindrical surfaces 16 and 17, respectively, and upper and lower extremities 18 and 19, respectively. Housing 15 may be fabricated of plastic or metal and may be of rigid or semi-rigid construction resistant to deformation by pressures encountered during normal use. A sealing cap 20 or other closure means is associated with said upper extremity.

A gas inlet port 21 is disposed within sealing cap 20. A short connector tube 22 extends upwardly from port 21. A gas conduit 23 is attached to connector tube 22 and extends upwardly to interaction with gas controller 11.

A groundwater inlet port 24 is disposed within said lower extremity 19. A first check valve 25 is associated with port 24 and is adapted to permit entrance of groundwater from said well into housing 15. The particular embodiment of valve 25 exemplified in the drawing is comprised of a fixed seating member 26 attached to interior surface 16, and an axially moveable member such as ball 27 configured to seat within seating member 26. Ball 27 has a density slightly greater than water, whereby the ball normally seats by gravity effect. However, upward flow of groundwater through port 24 is sufficient to lift ball 27, permitting flow into said housing. Water within said housing is prevented by valve 25 from flowing downwardly out of port 24. In alternative embodiments, the seating and moveable members of valve 25 may have a conical or other configuration of progressively diminishing circular cross section. Other types of valves may also be employed.

A second check valve 29 is disposed within housing 15 above said first check valve in a manner to divide said housing into an upper, activating chamber 30 bounded by sealing cap 20 and said second check valve, and a lower, sample accumulating chamber 31 bounded by said first and second check valves. Upper chamber 30 preferably has a total volume that is greater than the volume of lower chamber 31. The particular embodiment of check valve 29 exemplified in the drawing is comprised of a fixed seating member 32 attached to interior surface 16, and an axially moveable member 33 which floats in water and is provided with a bottom portion 34 configured to make close-fitting closure within seating member 32. The embodiment of moveable member 33 illustrated in FIGS. 1 and 2 is comprised of an upper float portion 35 and pendent bottom portion 34. The embodiment of moveable member 33 illustrated in FIG. 3 is of unitary construction which nevertheless provides the requisite flotation and properly configured bottom portion.

A sampling port 36 is located within said lower chamber adjacent and above said first check valve 25, and is provided with a hose coupling 37 outwardly emergent from exterior surface 17. Water-conveying conduit means in the form of tube 38 of narrow internal diameter attaches to coupling 37 and extends upwardly to an above-ground location. A third check valve 39 is associated with tube 38 in a manner to permit upward but not downward flow of water in said tube 38. Valve 39 may be located either adjacent the uppermost extremity of tube 38, as illustrated in FIGS. 1 and 2, or adjacent sampling port 36. The total inside volume of conduit means 38, whether in the form of a tube or other configuration, is smaller than the volume of upper chamber 30.

Figure 3:
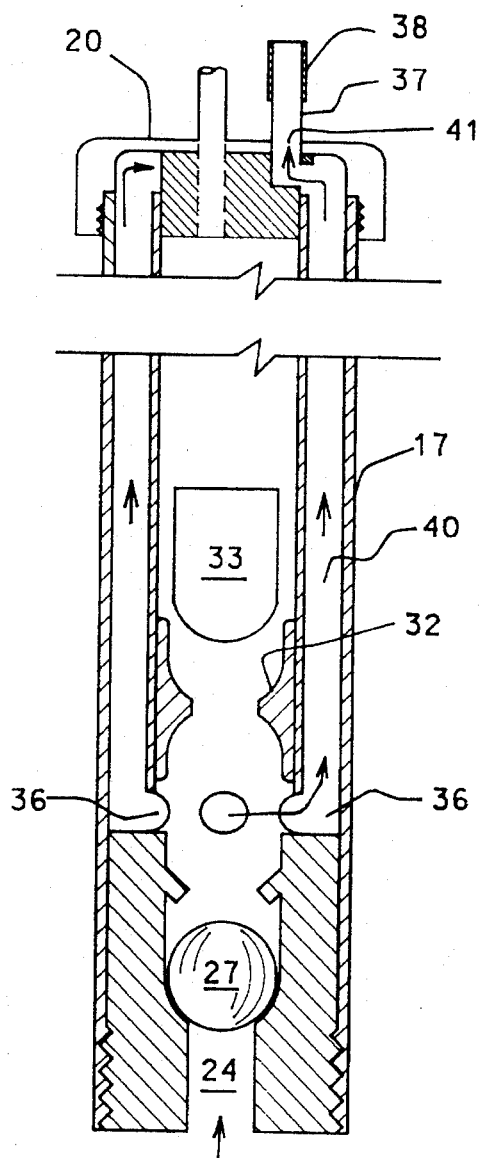
FIG. 3 is a fragmentary vertical sectional view of an alternative embodiment of the pumping apparatus of the present invention.

In the alternative embodiment of the pump assembly shown in FIG. 3, tube 38 at its lowermost extremity is an annular passageway 40 communicating between sampling ports 36 and a modified sealing cap provided with an auxiliary port 41. Hose coupling 37, now associated with port 41 of the modified sealing cap, receives tube 38. The flow of water takes the path indicated by the arrows in FIG. 3.

The pumping apparatus of this invention operates in a pulsed or cycled manner to elevate groundwater to an above-ground location. In the initial filling stage of the first cycle of pumping as shown in FIG. 1, the controller vents off through conduit 23 any pressurized gas communicating with the pump assembly. This enables hydrostatic pressure to drive water from the well through inlet port 24 to fill lower chamber 31 and enter upper chamber 30 and tube 38. Hydrostatic equilibrium is established when the level 42 in the well, the level 43 in upper chamber 30, and the level 44 in tube 38 are equal. In this condition, ball 27 is re-seated, ball 35 is floating, and the pump assembly is filled and ready to deliver water to the surface.

Gas controller 11 is programmed to supply to the pump assembly the necessary volume of pressurized gas from a compressor or bottled source to force the water in the pump assembly to the surface. The compressed gas, in the pumping stage of the cycle, travels by way of conduit 23 into upper chamber 30, where it exerts a pressure on surface level 43 of sufficient magnitude to cause: a) first check valve 25 to close, b) third check valve 39 to open, c) water within said housing to be driven upwardly through tube 38, and d) moveable member 33 of said second check valve to descend. When said moveable member, at its lowermost point of descent, seats within seating member 32, the pump assembly is in a sealed stage and ready to repeat the subsequent filling and pumping stages of the cycle. To initiate the next cycle of operation, the gas controller vents the pressurized gas through conduit 23. In situations where the hydrostatic pressure of the water in the well is insufficient to fill the housing, the gas controller may apply a vacuum to said upper chamber to augment the filling stage of operation. In a typical installation, the pumping rate for sampling purposes might be about 100 cc/minute, and might be adjustable to several gallons/minute for disposal purposes.

Because the interface 43 between the groundwater and the pressurized gas is far removed from said second check valve, the particular volume of groundwater driven upwardly through conduit means 38 in a given cycle is unaffected by any compositional alterations attributable to the interface.

To facilitate marketing, the pump assembly may be equipped with standardized hose fittings to permit easy attachment of conduit 23 and tube 38. In this manner, the relatively long lengths of said conduit and tube need not be packaged with the pump assembly, but can instead be provided by the user.

Figure 4:
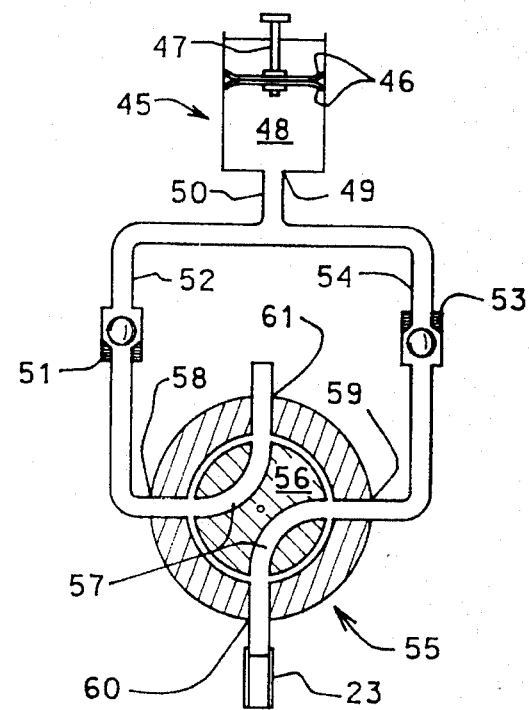
FIG. 4 is a schematic view of a gas controller useful as a component of the apparatus of FIG. 1, and shown in a first stage of operation.
Figure 5:
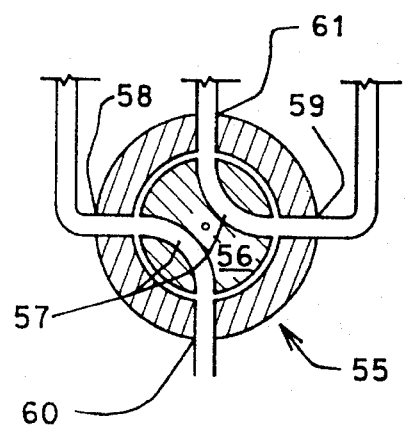
FIG. 5 is a fragmentary view of the gas controller of FIG. 4 shown in a second stage of operation.

A preferred type of gas controller useful in the pump apparatus of this invention is illustrated in FIG. 4. Said controller comprises a port 49 for receiving compressed gas, which may be provided by a piston-driven pump 45 of conventional design except that two cup seals 46 are attached to piston 47 in back-to-back relationship. When the piston travels within cylinder 48 toward port 49, gas is expelled from the cylinder. In the reverse direction of piston motion, gas is sucked into cylinder 48. A gas conduit 50 bifurcated into two paths forming a closed loop confines the gas from port 49. A first gas check valve 51 in first path 52 permits flow of gas toward but not away from port 49. A second gas check valve 53 in second path 54 permits gas flow away from but not toward port 49. A four port, ¼ turn rotary valve 55 whose rotor plug 56 has two separate passages 57 communicates with said two paths in a manner such that first path 52 enters the 9 o'clock port 58 and second path 54 enters the 3 o'clock port 59. In a first extreme position of rotor 56, as shown in FIG. 4, one route of free passage is established between 3 o'clock port 59 and 6 o'clock exit port 60, and a second route of free passage is simultaneously established between 9 o'clock port 58 and 12 o'clock venting port 61. In a second extreme position of rotor 56, shown in FIG. 5, one route of free passage is established between 12 o'clock port 61 and 3 o'clock port 59, and a second route of free passage is simultaneously established between 6 o'clock port 60 and 9 o'clock port 58. When rotor 56 is in neither extreme position, all passages through the rotor are closed. Exit port 60 communicates by way of gas conduit 23 with pump assembly 10.

In said first extreme position of rotor 56, when piston 47 travels toward outlet port 49, pressurized gas is routed to pump assembly 10. When piston 47 travels away from outlet port 49, first gas check valve 53 closes to preserve the downstream pressure in conduit 23, while check valve 51 opens to permit flow of intake air through port 61 and into cylinder 48.

In the second extreme position of rotor 56, when piston 47 travels toward outlet port 49, gas is expelled through check valve 53 and venting port 61. When piston 47 travels away from outlet port 49, air is drawn through conduit 23, ports 60 and 58 and check valve 51 into cylinder 48. Such action produces a reduced pressure or partial vacuum within housing 15, which augments entrance of groundwater. By virtue of its construction and mode of operation, a captive operating gas such as nitrogen can be used and retained by the system. This would be achieved by utilizing a reservoir vessel to confine the captive gas, supplying said captive gas to valve system 55 through port 61, and providing conduit means for returning said captive gas to said reservoir vessel.

The exemplified gas controller may be automated by use of suitable electric sensors and controls. Additional items such as gauges, relief valves, and vent valves can be added for particular applications.

In other applications, the pumping apparatus of the present invention may be employed in conventional situations where the disposal of water or other liquids to an elevated height or remote location is needed. Such applications include for example, removal of water from flooded building foundations, or underground conduits employed for communications, electrical cables or gas transport. Because no spark-producing electrical components are involved, the pump assembly of this invention is eminently suited for the handling of explosive liquids.

The pumping apparatus of this invention may be further automated by employing a gas controller capable of sensing an abrupt pressure change in tube 38. To do this, an easily constructed auxiliary valve would be placed so that it blocks off port 21 when liquid rises close to port 21 but not into tube 38. On the downward water flow, when floating valve bottom portion 34 is seated, there would be a pressure surge detectable by controller 11 so that rotor 56 and an additional escape valve opens. At the same time, rotor 56 is commanded to rotate ¼ turn to begin vacuumizing the pump. Conversely, when a negative vacuum is supplied to the pump, and port 21 is closed, controller 11 would receive a reverse command.

While particular examples of the present invention have been shown and described, it is apparent that changes and modifications may be made therein without departing from the invention in its broadest aspects. The aim of the appended claims, therefore is to cover all such changes and modifications as fall within the true spirit and scope of the invention.

Having thus described my invention, what is claimed is:

1. A pump assembly for the accurate transfer of water to an above ground elevation comprising:
   a) a tubular housing elongated upon a center axis and bounded by interior and exterior cylindrical surfaces and upper and lower extremities,
   b) a gas inlet port disposed in said upper extremity, and a gas conduit communicating between said gas inlet port and an above-ground location,
   c) a water inlet port disposed in said lower extremity, and a first check valve communicating with said water inlet port and permitting entrance of water upwardly into said housing,
   d) a second check valve disposed within said housing above said first check valve in a manner to divide said housing into an upper, actuating chamber bounded by said upper extremity and second check valve, and a lower, sample accumulating chamber bounded by said first and second check valves, said second check valve comprised of a seat member attached to the interior surface of said housing, and a floating member,
   e) a sampling port located within said lower chamber and communicating with a water-conveying conduit that extends to an above-ground location, and
   f) a third check valve disposed within said water-conveying conduit in a manner to permit upward flow but not downward flow of water within said water-conveying conduit.

2. A pumping apparatus comprising the pump assembly of claim 1 in combination with a gas controller member located above ground level and interactive with said gas conduit to supply a gas at controlled pressure, volume and timed intervals to the upper chamber of said housing.

3. The pumping apparatus of claim 2 wherein said gas conduit communicates with said gas controller.

4. The pump assembly of claim 1 wherein said first check valve is comprised of a fixed seating member attached to said interior surface, and an axially moveable member configured to seat within said seating member.

5. The pump assembly of claim 4 wherein said axially moveable member is a ball having a density greater than water.

6. The pump assembly of claim 1 wherein said second check valve is comprised of a fixed seating member attached to said interior surface, and an axially moveable member which floats in water and is provided with a bottom portion configured to make close-fitting closure with said seating member.

7. The pump assembly of claim 1 wherein the total inside volume of said water-conveying conduit is smaller than the volume of said upper chamber.

8. The pumping apparatus of claim 2 which operates in a cyclical, pulsed manner wherein the initial stage of a cycle causes pressurized gas in said gas conduit to be vented off.

9. The pumping apparatus of claim 8 comprising a pumping stage of said cycle whereby pressure is applied to said upper chamber, said pressure causing: a) said first check valve to close, b) said third check valve to open, and c) water within said housing to be driven upwardly through said water-conveying conduit.

10. The pumping apparatus of claim 2 wherein said gas controller is comprised of:
   a) an entrance opening for receiving a compressed gas,
   b) a gas conduit communicating with said entrance opening and bifurcated into first and second paths,
   c) a first check valve in said first path for permitting flow of gas toward but not away from said entrance opening,
   d) a second check valve in said second path for permitting flow of gas away from but not toward said entrance opening, and
   e) a quarter turn rotary valve having diametrically opposed first and second ports and diametrically opposed third and fourth ports, and equipped with a rotor having two separate passages, said first and second ports communicating with said first and second paths, respectively, said third port serving to vent gas, and said fourth port serving to supply compressed gas to said pump assembly.

* * * * *